United States Patent [19]

Corey

[11] Patent Number: 5,208,326
[45] Date of Patent: May 4, 1993

[54] 8-HYDROXY-2H-DIBENZ(B,F)AZEPIN-2-ONE DYES

[75] Inventor: Paul F. Corey, Elkhart, Ind.

[73] Assignee: Miles Inc., Elkhart, Ind.

[21] Appl. No.: 789,317

[22] Filed: Nov. 8, 1991

[51] Int. Cl.⁵ .......................... C12Q 1/37; C12Q 1/40; C07H 15/24; C08B 37/00
[52] U.S. Cl. ..................... 536/53; 536/18.7; 536/18.1; 530/331; 530/330; 546/165; 546/18
[58] Field of Search ............ 536/53, 18.7, 18.1; 530/330, 331; 546/165, 18; 514/19, 18, 17

[56] References Cited

U.S. PATENT DOCUMENTS

| | | | |
|---|---|---|---|
| 4,124,704 | 11/1978 | Scherrer | 536/53 |
| 4,433,139 | 2/1984 | Ogawa et al. | 536/53 |
| 4,442,284 | 4/1984 | Kolar et al. | 536/53 |
| 4,665,023 | 5/1987 | Deneke et al. | 546/165 |
| 4,716,222 | 12/1987 | Wallenfels et al. | 536/18.7 |
| 4,745,115 | 5/1988 | Markwell et al. | 514/232.8 |
| 4,810,636 | 3/1989 | Corey | 546/18 |
| 5,079,247 | 1/1992 | Tomcufcik et al. | 514/339 |
| 5,081,131 | 1/1992 | Tomcufcik et al. | 514/339 |
| 5,104,980 | 4/1992 | Corey | 536/18.1 |
| 5,108,890 | 4/1992 | Wielinger et al. | 530/330 |

*Primary Examiner*—Ronald W. Griffin
*Assistant Examiner*—Louise N. Leary
*Attorney, Agent, or Firm*—Jerome L. Jeffers

[57] ABSTRACT

Disclosed are 8-Hydroxy-2H-dibenz[b,f]azepin-2-one dyes, chromogenic enzyme substrates made from them and methods for preparing the same.

11 Claims, No Drawings

8-HYDROXY-2H-DIBENZ(B,F)AZEPIN-2-ONE DYES

BACKGROUND OF THE INVENTION

The present invention involves 8-hydroxy-2H-dibenz[b,f]azepin-2-one dyes which are useful as acid/base indicators and which serve as chromogenic substrates for hydrolytic enzymes. The substrates have superior optical properties and can be used to measure low levels of enzyme concentration.

2,8-disubstituted dibenz[b,f]azepines are known, but only 8 members of this class of compound are reported in the literature. There are also 8 known 2H-dibenz[b,f]azepin-2-ones:
2H-dibenz[b,f]azepin-2-one
1-chloro-2H-dibenz[b,f]azepin-2-one
1-bromo-2H-dibenz[b,f]azepin-2-one
1-nitro-2H-dibenz[b,f]azepin-2-one
3,6,10-trihydroxy-2H-dibenz[b,f]azepin-2-one
1-acetyl-3,6,10-trihydroxy-2H-dibenz[b,f]azepin-2-one
10,11-dihydro-2H-dibenz[b,f]azepin-2-one
4,6,8-tribromo-10,11-dihydro-2H-dibenz[b,f]azepin-2-one The last is the only reported 8-substituted 2H-dibenz[b,f]azepin-2-one. Its synthesis was described by Teuber and Schmidtke [*Chem. Ber.* 93, 1257 (1960)]. None of the 2H-dibenz[b,f]azepin-2-ones listed above are pH indicators, although some may be colored.

It is an object of the present invention to provide novel 8-substituted 2H-dibenz[b,f]azepin-2-ones which are suitable for use as acid/base indicators. Incorporation of an ionizable hydroxyl group into the 8-position affords such indicator compounds. It is also an object of the present invention to derivatize said acid/base indicator compounds with suitable enzymatically cleavable groups so as to provide chromogenic substrates for hydrolase enzymes.

SUMMARY OF THE INVENTION

The present invention involves 2,8-disubstituted 2H-dibenz[b,f]-azepine based compounds characterized by the formula:

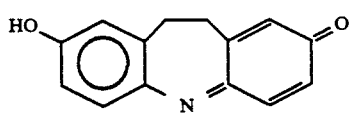

In the above formula X is $CH_2CH_2$ or $CH=CH$ and Y is H or an enzyme cleavable group.

DESCRIPTION OF THE INVENTION

The present invention involves a new class of dyes useful as pH indicators and colorimetric enzyme substrates. These dyes possess the 2H-dibenz[b,f]azepin-2-one ring system and are represented in their simplest forms by structures 1 and 2:

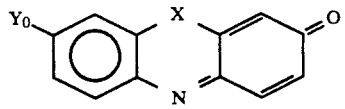

1

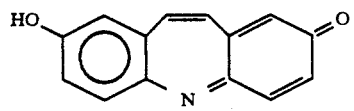

2

Structure 1 is 8-hydroxy-2H-dibenz[b,f]azepin-2-one, a pH indicator that is salmon colored in acid (pH = 4.98, 456 nm, $\epsilon = 7,270$), magenta in base (pH = 7.8, 574 nm, $\epsilon = 70,250$) and has a pKa of 6.34. Structure 2 is 8-hydroxy-10,11-dihydro-2H-dibenz[b,f]azepin-2-one, a pH indicator that is yellow in acid (pH = 4.5, 478 nm, $\epsilon = 19,760$) blue in base (pH = 10.61, 602 nm, $\epsilon = 65,000$) and has a pKa of 6.95.

Related dyes may be prepared by replacing the hydrogen atom on the aromatic ring of 1 or 2 with a variety of functional groups. Thus, when Y is not H in the foregoing general formula, it can represent an enzyme cleavable group which is selected to confer specificity to a specific corresponding enzyme of analytical interest. Thus, the enzyme cleavable group Y is a radical of a compound Y—OH comprising an enzyme specific moiety which can be selected to confer specificity to any one of a wide variety of enzymes, particularly hydrolases, and includes, for example, enzyme specific moieties such as sugars and derivatives thereof, acyl groups including aliphatic and aromatic carboxylic acids, amino acids and peptides together with inorganic acids such as phosphoric and sulfuric acids. Accordingly, the present invention provides a useful acid/base indicator and can also be used in the detection of various enzymes of clinical interest when the indicators are derivatized with an appropriate enzyme cleavable group Y.

When Y is cleaved by a specific enzyme therefore in a basic solution, pH 7 to 11, a deprotonated form of the chromogen is liberated which has an absorbance maximum which is substantially greater than the absorbance maximum of the uncleaved chromogenic enzyme substrate of the present invention. The distinct change in absorbance provides a readily observable and detectable optical signal which can be accurately measured and correlated to the amount of enzyme present in a liquid test sample.

The readily visualized color change between the acid and base forms of these dyes, together with their low pKa's and large extinction coefficients, makes them particularly well suited to incorporation into colorimetric substrates for hydrolase enzymes. For example, the corresponding β-D-galactopyranosides (in which Y is β-D-galactopyranose) 3 and 4 are excellent chromogenic substrates for β-galactosidase (E.C.3.2.1.23), a glycosidase commonly used as an indicator enzyme in immunoassays.

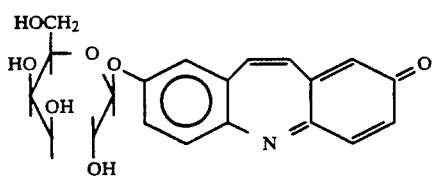

3

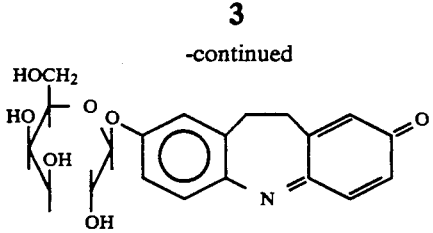

Similar derivatization of 1 and 2 with other enzyme cleavable groups will give rise to other chromogenic substrates for other hydrolases. These substrates can be incorporated into test devices as colorimetric indicators for the detection and quantitation of specific hydrolases.

Preparation of the indicator compounds of the present invention is illustrated in Scheme I.

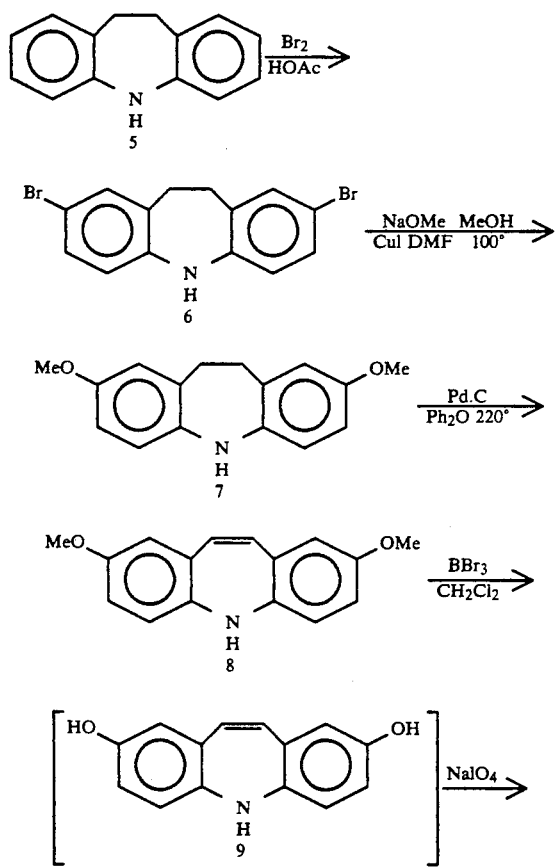

Referring to Scheme I, the synthesis of 1 from commercially available iminodibenzyl (5) is illustrated. Thus, 2,8-Dibromoiminodibenzyl (6) is first prepared from (5) according to the procedure of Kricka and Ledwith, *J. Chem. Soc. Perkin I*, 859 (1973). Treatment of 6 with a large excess of sodium methoxide [method of Hseih and Litt, *Macromolecules* 19, 516 (1986)]affords good yields of 2,8-dimethoxyiminodibenzyl (7). Dehydrogenation of 7 to give 2,8-dimethoxy-5H-dibenz[b,-f]azepine (8) is accomplished in modest yields by heating at 200° C. with palladium on carbon. Cleavage of the methyl ethers with BBr₃ in CH₂Cl₂ gives a nearly quantitative conversion to the diol (9) which is not isolated but rather immediately oxidized with sodium periodate to the desired product (1).

Scheme II outlines the synthesis of 2 from iminodibenzyl (5). The route is similar to that of Scheme I except that 2,8-dimethoxyiminodibenzyl (7) is demethylated to give diol 10 and then immediately oxidized to give the desired chromogen 2.

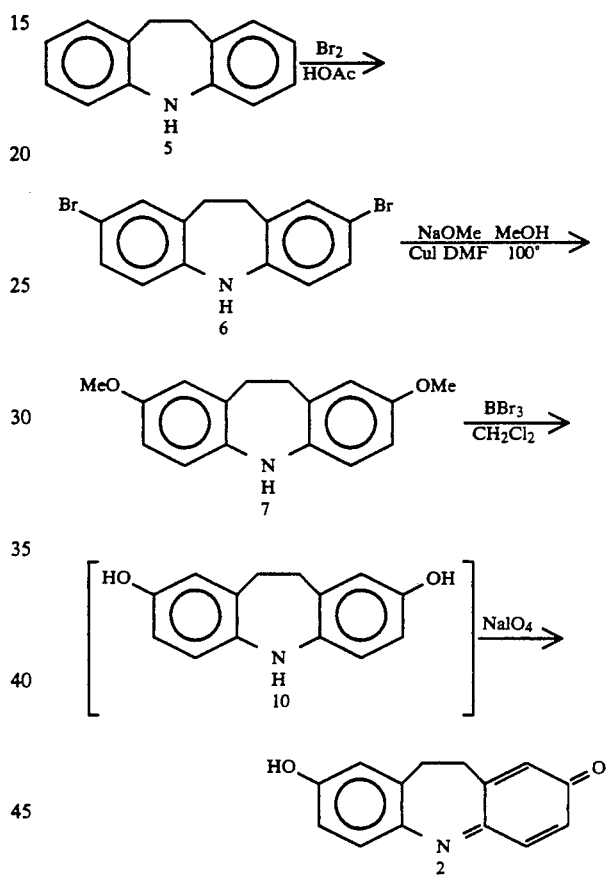

The steps in the synthesis of the β-galactoside of 1 are set out in Scheme III.

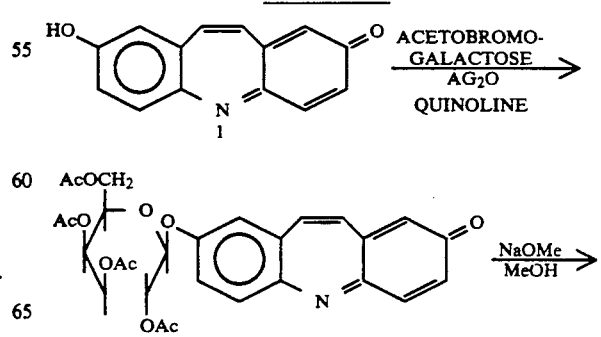

-continued
Scheme III

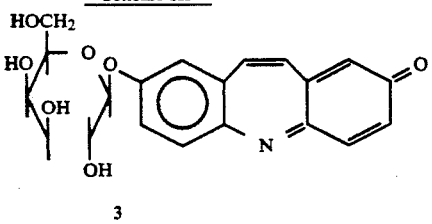

3

Referring to Scheme III, the dye is reacted with acetobromogalactose and silver (I) oxide in quinoline overnight to give the protected galactoside 11 in good yield. Hydrolysis of the protecting groups with sodium methoxide in methanol provides 8-$\beta$-D-galactopyranosyloxy-2H-dibenz[b,f]azepin-2-one (3), a novel chromogenic $\beta$-galactosidase chromogen. The synthesis of the $\beta$-galactosidase of 2 is essentially the same.

The aromatic, carbocyclic and heterocyclic rings of the present compounds can bear a variety of substituent groups without departing from the scope of the invention. Such substituent groups are limited only by the ability of one skilled in this art to prepare stable compounds which have the chromogenic enzyme substrate properties desired, and include such groups as substituted and unsubstituted alkyl, substituted and unsubstituted aryl, alkoxy, aryloxy, halo (e.g. fluoro, chloro and bromo), nitro and substituted amino such as dialkylamino.

When Y is H in the chromogenic compounds of the present invention, they are useful as pH indicators. When they are derivatized to chromogenic substrates, i.e. Y is converted to an enzyme cleavable moiety and contacted with the enzyme in solution having a pH of from about 7 to 11, the enzymatically cleavable group Y is cleaved by the enzyme to liberate the dissociated form of the chromogen which has an absorbance maximum which is substantially greater than the absorbance maximum of the chromogenic enzyme substrate to provide a distinct change in their relative absorbance maxims. Accordingly, the compounds of the present invention, when Y is an enzyme cleavable group, are particularly useful in an analytical test system which requires the detection of an enzyme-labeled assay reagent employed therein. The distinct and measurable change in the absorbance maximum which is generated between the substrate compound and the enzymatically cleaved form of the chromogen can be accurately detected, measured and correlated to the amount of analyte present in a liquid test sample.

According to the present invention, the Y group is either H, when the chromogens are to be used as acid/base indicators or an enzyme specific moiety to provide novel chromogenic enzyme substrate compounds which confer specificity to a wide variety of enzymes encountered in analytical clinical chemistry, particularly the hydrolase enzymes. The selection of a particular enzymatically cleavable group Y will depend upon the particular enzyme of interest. For example, where the particular enzyme of interest is a glycosidase, a glycoside can be prepared in which the Y group is the glycosidic radical corresponding to the natural substrate for the particular glycosidase, e.g. mono- and oligosaccharide radicals which are capable of being incorporated into a glycoside substrate specific for a particular glycosidase enzyme and cleaved by said enzyme such as radicals of $\beta$-D-galactopyranose, $\alpha$-D-galactopyranose, $\beta$-D-glucopyranose, $\alpha$-D-glucopyranose and $\alpha$-D-maunopyranose as well as amino sugars such as N-acetylglucosamine and N-acetylneuraminic acid. Other suitable glycosidic radicals include oligosaccharide chains from between about 2 to 20, preferably 2 to 7 monosaccharide units attached by $\alpha$-1-4 glucosidic linkages which can be broken down by saccharide chain splitting enzymes to a mono- or oligosaccharide such as radicals of maltopentose, maltohexose and maltoheptose which can, in turn, be cleaved by a corresponding glycosidase.

Selection of the enzymatically cleavable group Y will depend, of course, upon the particular enzyme of interest. Thus, in the case of non-specific esterase enzymes, the enzymatically cleavable group Y is an acyl radical group to provide a chromogenic ester of the formula:

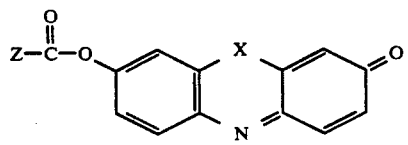

where Z is lower alkyl or aryl which can be used to detect the presence of nonspecific esterase enzymes such as cholinesterase, acylase or lipase. The chromogenic enzyme substrate compounds of the present invention can also be utilized for the detection of proteolytic enzymes commonly found in leukocytes. Such compounds are esters of the general formula 1 or 2 where H is replaced by a radical Y of the compound Y—OH and where Y—OH is an N-protected amino acid, e.g., N-tosyl-L-alanine, or a short peptide, e.g. consisting of between about 2 to 5 amino acid units.

Similarly, for the detection of alkaline phosphatase in a liquid test sample, the enzymatically cleavable group Y is a radical of the compound Y—OH wherein Y—OH is a phosphoric acid group to provide a chromogenic phosphate ester of the formula:

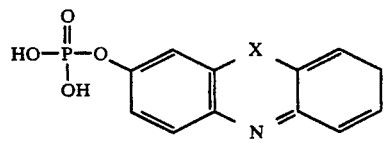

The chromogenic enzyme substrate compounds of the present invention are useful in analytical test systems which require the measurement of the amount of enzyme present therein, particularly those analytical test systems employing enzyme labeled assay reagents. Such analytical test systems include, for example, enzyme immunoassays known as competitive, sandwich and immunometric techniques where the amount of enzyme label in a particular fraction thereof can be measured and correlated to the amount of analyte under determination which is obtained from a liquid test sample. The use of specific binding substances, such as antigens, haptens, antibodies, lectins, receptors, avidin and other binding proteins and polynucleotides labeled with the enzyme have been developed and applied to the measurement of substances in biological fluids. Generally, such measurements depend on the ability of a binding substance, e.g. an antibody or an antigen, to bind to a specific analyte wherein a labeled reagent comprising such binding substance labeled with an enzyme is employed to determine the extent of such binding. Typically, the extent of binding is determined by measuring the amount of enzyme label present in the labeled reagent wherein the amount of enzyme detected can be correlated to the amount of analyte present in the liquid test sample.

The chromogenic enzyme substrate compounds of the present invention are particularly useful in analytical test systems where an analytical test device comprising a carrier matrix impregnated with the chromogenic enzyme substrate compound is employed wherein the nature of the enzyme specific moiety depends on the particular enzyme being detected. The carrier matrix can be of any substance capable of being impregnated with the present chromogenic enzyme substrate compound such as those used for reagent strips for solution analysis. Examples of such materials include felt, porous ceramic strips as well as woven or matted glass fibers. Alternatively, wood sticks, cloth, sponge material, synthetic resin fleeces and glass fiber felts can be used as the matrix material. Preferably, the carrier matrix is a bibulous material, such as filter paper, which is impregnated with the chromogenic enzyme substrate compound by contacting the bibulous material with a solution thereof.

In a preferred embodiment, the carrier matrix is a bibulous material in the form of a zone or layer incorporated with the chromogenic enzyme substrate compound which is employed where a particular assay is performed in a liquid environment employing an insoluble assay reagent known in the art to physically separate the free species of the labeled reagent from the bound species of the labeled reagent. In carrying out such an assay system, an aliquot of liquid containing the free species is removed and applied to the carrier matrix wherein the chromogenic enzyme substrate compound incorporated therein interacts with the enzyme label of the labeled reagent of the free species from the liquid test sample to provide a detectable color change which can be visibly observed and/or measured with an appropriate instrument such as a spectrophotometer.

The method of practicing the present invention is further illustrated by the following examples:

EXAMPLE I

Compound Preparation a. 2,8-Dimethoxy-10,11-dihydro-5H-dibenz[b,f]azepine (7)

A solution of sodium metal (23 g; 1 mol) in anhydrous methanol (250 mL) was treated with dimethylformamide (DMF) (125 mL; dried over molecular sieve 4A), copper(I) iodide (38 g; 199.5 mmol), 2,8-dibromo-10,11-dihydro-5H-dibenz[b,f]azepine (6) (17.9 g; 50.7 mmol) [L. Kricka and A. Ledwith, *J. Chem. Soc. Perkin I*, 859 (1973)]and additional DMF (125 mL). The mixture was mechanically stirred and heated (mantle) at reflux (internal temperature was 92° C.) for four hours. After cooling to ca. 35° C. the copper-colored mixture was filtered through Celite (Johns-Manville Corp., Denver, CO, USA) and the cake was washed with ethyl acetate (EtOAc; 500 mL). The combined filtrate and wash were blended into H$_2$O (2 L) and the phases separated. The aqueous layer was extracted twice with EtOAc (500 mL each) then the combined EtOAc layers were washed once with H$_2$O (500 mL), once with brine (saturated aqueous NaCl; 500 mL) and dried over a mixture of MgSO$_4$ (50 g) and Darco G-60 (ICI Americas, Inc., Wilmington, DE, USA; 20 g). The solution was filtered through Celite and concentrated in vacuo to a total volume of 40–50 mL. The concentrate was heated to boiling, diluted with hexane (ca. 60 mL) and allowed to cool to ambient temperature overnight whereupon the title compound (7) (7.04 g) separated as beige plates; the mother liquor was worked for a second crop (1.68 g; total yield 67.6%). A portion of the first crop was sublimed (0.1 torr; 122–4° C. bath) to afford the analytical sample as white plates with mp=123–4° C.: IR (KBr) cm$^{-1}$ 3390, 2946, 1510, 1262, 1221, 1039, 1031, 911, 852, 810; $^1$H NMR (300.12 MHz) (DMSO-d$^6$) δ2.90 (s, 4H), 3.64 (s, 6H), 6.55–6.65 (m, 4H), 6.83 (d, J=8.5 Hz, 2H), 7.64 (s, 1H); $^{13}$C NMR (75.47 MHz) (DMSO-d$^6$) ppm 151.9, 137.6, 128.7, 118.7, 115.2, 112.5, 55.2, 34.3; mass spectrum m/e 255, 240 (base), 225, 209, 197, 180, 168.

*Anal.* calcd. for C$_{16}$H$_{17}$NO$_2$: C, 75.27; H, 6.71; N, 5.49. Found: C, 75.31; H, 6.54; N, 5.40.

b. 2,8-dimethoxy-5H-dibenz[b,f]azepine (8)

2,8-Dimethoxy-10,11-dihydro-5H-dibenz[b,f]azepine (7) (3.0 g; 11.75 mmol) and 10% palladium on carbon (3.0 g) were taken up in diphenyl ether (100 mL) and heated in a 220–222° C. oil bath for 2 days while a slow stream of CO$_2$ gas bubbled through the mixture. The reaction was cooled and filtered through Celite, then the diphenyl ether was removed by kugelrohr distillation (0.1 torr; 110–120° C.) leaving an orange crystalline residue (2.52 g). The bulk of unreacted 7 was removed by crystallization from a minimum of CHCl$_3$/hexane (1:3) which afforded the title compound (8) (0.88 g; 29.5%) as fluffy yellow plates. A portion was chromatographed on a silica gel column developed with CHCl$_3$ then crystallized as above to afford the analytical sample with mp=204.5–205.5° C.: IR (KBr) cm$^{-1}$ 3360, 1598, 1500, 1474, 1265, 1227, 1035, 862, 813; $^1$H NMR (CDCl$_3$) δ3.73 (s, 6H), 4.77 (v. br. s, 1H), 6.4–6.7 (m, 8H); $^{13}$C NMR (DMSO-d$^6$) ppm 154.6, 143.3, 132.4, 130.3, 119.9, 115.3, 114.6, 55.2; mass spectrum, m/e 253 (base), 238, 210, 167.

Anal. calcd. for C$_{16}$H$_{15}$NO$_2$: C, 75.87; H, 5.97; N, 5.53. Found: C, 76.07; H, 6.31; N, 5.37.

c. 8-Hydroxy-2H-dibenz[b,f]azepin-2-one (1)

A solution of 2,8-dimethoxy-5H-dibenz[b,f] azepine (8) (1.0 g; 3.95 mmol) in warm CH$_2$Cl$_2$ (23.5 mL, dried over molecular sieve 4A), maintained under a CaSO$_4$ drying tube, was cooled in an ice bath (8 separates as a fine suspension) and treated with BBr$_3$ (1.85 mL; 19.6 mmol; 5 eq). The mixture immediately turned blue and became homogeneous. The ice bath was removed after 5 minutes and the reaction was stirred at ambient temperature for 3.5 hours. The mixture was carefully blended into H$_2$O (350 mL) (HBr evolution!) and extracted four times with EtOAc (100 mL each). The combined EtOAc layers were washed with brine (100 mL) then transferred to a 3-neck round bottom flask and rapidly mechanically stirred with a solution of NaIO$_4$ (3.0 g) in H$_2$O (100 mL) for 15 minutes. During this time the reaction turned dark red-brown and a solid separated. The mixture was filtered and the collected solids were washed liberally with H$_2$O and EtOAc then dried to give the title compound (1) (0.76 g; 86%). A portion was recrystallized from boiling DMF then vacuum dried at 130° C. to afford the analytical sample as fine black whiskers with mp=239–41° C. (dec.): IR (KBr) cm$^{-1}$ 3475, 1600, 1555, 1538, 1453, 1340, 1270, 1230, 1115, 885, 895, 795; $^1$H NMR (DMSO-d$^6$) δ6.85 (br. s, 2H), 6.95–7.08 (m, 4H), 6.66 (br. d, J=7.5 Hz, 2H); mass spectrum, m/e 223, 195 (base), 178, 166; $\lambda_{max}$=456 nm (7,270) (pH=4.98; 0.1 M acetate) $\lambda_{max}$=574 nm (70,250) (pH=7.8; 0.1 M borate), $pK_a$=6.34.

Anal. calcd. for $C_{14}H_9NO_2$: C, 75.32; H, 4.06; N. 6.2. Found: C, 74,98; H, 4.35; N, 6.54.

d. 8-Hydroxy-10,11-dihydro-2H-dibenz[b,f]azepin-2-one (2)

A solution of 2,8-dimethoxy-10,11-dihydro-5H-dibenz[b,f]azepine (7) (1.0 g; 3.9 mmol) in $CH_2Cl_2$ (23.5 mL; dried over molecular sieve 4A), maintained under a $CaSO_4$ drying tube, was cooled to 0° C. and treated with $BBr_3$ (1.85 mL; 19.6 mmol; 5 eq). After 5 minutes the reaction was warmed and allowed to stir at ambient temperature for 3.75 hours. The mixture was carefully blended into $H_2O$ (350 mL) and this was then extracted four times with EtOAc (100 mL each). The combined EtOAc layers were washed with brine (50 mL) then transferred to a 3-neck round bottom flask equipped with a mechanical stirrer and rapidly stirred for 15 minutes with a solution of $NaIO_4$ (3.0 g) in $H_2O$ (200 mL). The phases were separated and the aqueous layer was washed with EtOAc (25 mL). The combined EtOAc layers were washed four times with $H_2O$ (100 mL each) then the combined $H_2O$ washes were back-washed with EtOAc (50 mL). The combined EtOAc layers were then washed with brine (100 mL), dried over $Na_2SO_4$ and evaporated to dryness under reduced pressure. The residue was taken up in hot EtOAc (ca. 150 mL), concentrated by boiling to ca. 50 mL and diluted with hexane (20 mL). Upon cooling the title compound (2) separated as a red powder that was isolated by filtration and vacuum dried overnight at 60° C. The yield after two crops was 0.80 g (90%); the first crop was analytically pure and decomposed at temperatures above 200° C., the exact decomposition point dependant upon the rate of heating: IR (KBr) cm$^{-1}$ 1630, 1612, 1556, 1480, 1463, 1295, 1222, 1207, 1107, 888, 827; $^1$H NMR (DMSO-d°) $\delta$2.77 (br. s, 4H), 6.2-6.9 (v. br. m, 4H), 7.1-7.5 (v. br. m, 2H), 10.43 (br. s, 1H); $^{13}$C NMR (DMSO-d$^6$) ppm 186.9, 160.6, 160.4, 151.5, 146.4, 144.9, 138.4, 137.6, 129.4, 128.2, 116.0, 114.9, 33.1, 31.2; mass spectrum, m/e 225 (base), 196. 167; $\lambda_{max}$=478 nm (19,760) (pH=4.5; 0.1 M acetate) $\lambda$max=602 nm (65,000) (pH=10.61; 0.1 M glycine), $pK_a$=6.95.

Anal. calcd. for $C_{14}H_{11}NO_2$: C, 74.65; H, 4.92; N, 6.22. Found: C, 74.54; H, 4.88; N, 5.84.

e. 8-(Tetra-O-acetyl-β-D-galactopyranosyloxy)-2H-dibenz[b,f]azepin-2-one (11)

A mixture of 8-hydroxy-2H-dibenz[b,f]azepin-2-one (1) (0.558 g; 2.5 mmol), acetobromogalactose (1.645 g, 1.6 eq) and silver(I) oxide (0.927 g; 1.6 eq) in anhydrous quinoline (18 mL) were stirred for 15.3 hours in a tightly stoppered flask protected from light. The reaction was filtered through Celite, diluted with EtOAc (60 mL) and extracted twice with aqueous 1.25 M HCl (100 mL each). The combined HCl extracts were washed twice with EtOAc (50 mL each) then the combined EtOAc layers were washed with brine (100 mL), dried over $Na_2SO_4$, filtered and evaporated to dryness under reduced pressure to give a red-orange foam (2.10 g). This was chromatographed on silica gel (200 g, 5 cm ID column), using 9% acetone in chloroform solvent, and the red-orange product band was collected and freed of solvent in vacuo to give a red glass (1.51 g). Crystallization from EtOAc/hexane afforded the title compound (11) (1.03 g, 75%) as a red-orange powder. One recrystallization from EtOAc/hexane gave the analytical sample with mp=151.5-152.5° C.: IR (KBr) cm$^{-1}$ 1758, 1630, 1521, 1372, 1225, 1076; $^1$H NMR (DMSO-d$^6$) $\delta$7.90 J=9.6 Hz, 1H), 7.54 (d, J=9.9 Hz, 1H), 7.30-7.36 (m, 2H), 7.08 (AB, $J_A$=29 Hz and $J_B$=12.0 Hz, 2H), 6.92 (d of d, $J_1$=2.3 Hz and $J_2$=9.9 Hz, 1H), 6.67 (d, J=2.2 Hz, 1H), 5.73 (d, J=7.4 Hz, 1H), 5.39 (br. s, 1H), 5.23-5.33 (m, 2H), 4.51 (t, J=6.2 Hz, 1H), 4.11 (d, J=6.3 Hz, 2H), 2.16 (s, 3H), 2.06 (s 3H), 2.01 (s, 3H), 1.96 (s, 3H); $^{13}$C NMR (DMSO-d$^6$) ppm 185.4, 170.0, 169.9, 169.6, 169.3, 158.6, 151.5, 144.1, 141.0, 139.4, 139.2, 135.3, 134.3, 134.0, 133.6, 126.9, 118.8, 97.0, 70.8, 70.2, 68.2, 67.2, 61.4, 20.5 (3 redundant and 1 coincident bands).

Anal. calcd for $C_{20}H_{27}NO_{11}$: C, 60.75; H, 4.63; N, 2.53. Found: C, 60.75; H, 4.98; N, 2.50.

f. 8-(β-D-galactopyranosyloxy)-2H-dibenz[b,f]azepin-2-one (3)

A solution of 8-(tetra-O-acetyl-β-D-galactopyranosyloxy)-2H-dibenz[b,f]azepin-2-one (11) (1.12 g; 2.02 mmol) in absolute methanol (MeOH), warmed in a 55° C. bath, was treated with sodium methoxide (50 mg) and stirred for 1.3 hours under an argon blanket; during this time a solid separates. The reaction was freed of solvent under reduced pressure and the residue was crystallized from hot DMF/EtOH (5:1). The title compound (3) (0.498 g; 63%) was obtained in two crops as a brick-red wool that decomposed at temperatures over 230° C. The first crop was vacuum dried at 130° C. for 6 hours to afford the analytical sample: IR (KBr) cm$^{-1}$ 3416, 3269, 2884, 1632, 1607, 1574, 1540, 1503, 1347, 1267, 1234, 1083, 1032, 895; $^1$H NMR (DMSO-d$^6$) $\delta$7.87 (d, J=9.6 Hz, 1H), 7.57 (d, J=10.0 Hz, 1H), 7.34-7.41 (m, 2H), 7.10 (AB, $J_A$=31.9 Hz and $J_B$=12.0 Hz, 2H), 6.92 (d of d, $J_1$=1.7 Hz and $J_2$=9.5 Hz, 1H), 6.67 (d, J=1.9 Hz, 1H), 5.29 (v. br. s, 1H), 5.08 (d, J=7.6 Hz, 1H), 4.45-5.00 (v. br. m, 2H), 3.40-3.76 (m, 7H); $^{13}$C NMR (DMSO-d$^6$) ppm 185.3, 160.2, 144.0, 140,3, 139.5, 139.1, 135.6, 134.2, 133.7, 133.3, 126.5, 119.2, 118.5, 100.6, 75.8, 73.3, 70.2, 68.1, 60.3.

Anal. calcd. for $C_{20}H_{19}NO_7$: C, 62.33; H, 4.97; N, 3.64. Found: C, 62.53; H, 5.13; N, 3.73.

g. 8-(Tetra-O-acetyl-β-D-galactopyranosyloxy)-10,11-dihydro-2H-dibenz[b,f]azepin-2-one (12)

A mixture of 8-hydroxy-10,11-dihydro-2H-dibenz[b,f]azepin-2-one (2) (0.2252 g; 1.0 mmol), acetobromogalactose (0.6579 g; 1.6 eq) and silver(I) oxide (0.3708 g; 1.6 eq) in anhydrous quinoline (7.5 mL) was stirred in a tightly stoppered flask protected from light for 22.5 hours. The reaction was filtered through Celite, diluted with EtOAc (100 mL) and extracted twice with aqueous 1.0 M HCl (100 mL each). The combined HCl extracts were washed with EtOAc (20 mL) then the combined EtOAc layers were washed with brine (50 mL), dried over $Na_2SO_4$, filtered and evaporated to dryness in vacuo to give a red-orange tar (0.82 g). This was chromatographed on silica gel (75 g; 3 cm ID column), using 13% ethyl ether ($Et_2O$) in chloroform solvent, and the red-orange product band was collected and evaporated to dryness under reduced pressure to give an orange foam (0.54 g) which was crystallized from EtOAc/hexane (1:1). The title compound (12) (0.45 g; 85%) was obtained in two crops as an orange wool with mp=137-8° C.: IR (KBr) cm$^{-1}$ 1754, 1641, 1615, 1510, 1371, 1230, 1077; $^1$H NMR (CDCl$_3$) $\delta$7.58 (d, J=8.75 Hz, 1H), 7.26 (d, J=9.9 Hz, 1H), 6.97 (d of d, J$_1$=2.8 Hz and J$_2$=8.75 Hz, 1H), 6.80 (d, J=2.8 Hz, 1H), 6.59 (d of d, J$_1$=2.2 Hz and J$_2$=9.9 Hz, 1H), 6.27 (d, J=2.1 Hz, 1H), 5.47-5.55 (m, 2H), 5.10-5.18 (m, 2H), 4.09-4.30 (m, 3H); $^{13}$C NMR (DMSO-d$^6$) ppm 187.0, 170.0, 169.9, 169.6, 169.3, 157.4, 153.3, 146.2, 145.0, 141.3, 138.0, 136.2, 130.2, 128.8, 116.6, 114.8, 97.0, 70.6, 70.2, 68.2, 67.3, 61.5, 33.2, 30.8, 20.5 (3 coincident bands).

Anal. calcd. for C$_{28}$H$_{29}$NO$_{11}$: C, 60.53; H, 5.26; N, 2.52. Found: C, 60.16; H, 5.36; N, 2.62.

h.

8-($\beta$-D-galactopyranosyloxy)-10,11-dihydro-2H-dibenz[b,f]azepin-2-one (4)

A solution of 8-(tetra-0-acetyl-$\beta$-D-galactopyranosyloxy)-10,11-dihydro-2H-dibenz[b,f]azepin-2-one (12) (0.38 g; 0.69 mmol) in absolute MeOH (27.5 mL) was treated with sodium methoxide (17.7 mg) then stirred in a 50° C. bath for 1 hour under an Argon blanket; during this time a solid separates. The reaction was cooled in ice, neutralized with glacial acetic acid (22 $\mu$L) and allowed to stand for 1 hour. The solid was filtered, washed twice with ice-cold MeOH then vacuum dried to give the analytically pure title compound (4)(0.216 g; 81%) as an orange powder which decomposes at temperatures above 220° C: IR (KBr) cm$^{-1}$ 3330, 2910, 1640, 1605, 1500, 1315, 1255, 1230, 1085, 887; $^1$H NMR (DMSO-d$^6$) $\delta$7.52 (d, J=8.7 Hz, 1H), 7.25 (d, J=9.9 Hz, 1H), 7.03 (d of d, J$_1$=2.8 Hz and J$_2$=8.7 Hz, 1H), 6.95 (d, J=2.8 Hz, 1H), 6.54 (d of d, J$_1$=2.3 Hz and J$_2$=9.9 Hz, 1H), 6.32 (d, J=2.3 Hz, 1H), 5.19 (d, J=5.2 Hz, 1H), 4.93 (d, J=7.7 Hz, 1H), 4.88 (d, J=5.7 Hz, 1H), 4.66 (t, J=5.4 Hz, 1H), 4.52 (d, J=4.6 Hz, 1H), 3.70 (br. t. J=3.8 Hz, 1H), 3.37-3.66 (m, 5H), 2.74-2.91 (br. m, 4H); $^{13}$C NMR (DMSO-d$^6$) ppm 187.0, 159.0, 152.7, 146.3, 145.0, 140.6, 137.8, 136.4, 129.9, 128.6, 116.6, 115.0, 100.7, 75.7, 73.3, 70.2, 68.2, 60.4, 33.3, 31.0.

Anal. calcd. for C$_{20}$H$_{21}$NO$_7$: C, 62,01; H, 5.46; N, 3.62. Found: C, 61.76; H, 5.32; N, 3.51.

EXAMPLE II

Substrate Evaluation

Compound 4 is a substrate for $\beta$-galactosidase and exhibits Michaelis-Menten kinetics. In the presence of $\beta$-galactosidase, a solution of 4 in 50 mM phosphate buffer pH 7.4 (containing no magnesium) was hydrolyzed to give 2 at a rate (K$_{cat}$) of 7.07$\times$10$^3$ mol. min$^{-1}$/mol. active site and exhibited a Km of 0.096 mM.

Compound 3 is also a substrate for $\beta$-galactosidase, and a test device sensitive to the presence of this enzyme was prepared. The device comprised a small rectangular piece of filter paper mounted at one end of an oblong strip of polystyrene film. The paper was impregnated with various ingredients, including 3, a buffer and an inorganic salt. A 2 inch wide strip of Whatman CCP500 filter paper was immersed in an aqueous solution containing the following:

0.3 M Bicine buffer pH=7.4
4.0 mM MgCl$_2$

The paper was dried and then immersed in a dimethylformamide (DMF) solution containing 5.0 mM of compound 3. The paper was again dried to provide a salmon-colored test paper. A piece of the dried, impregnated paper was cut into a 0.2 inch$\times$0.4 inch rectangle and mounted at one end of an axially oriented polystyrene strip measuring 0.2 inch$\times$3.25 inch using double-faced adhesive.

The test papers were dipped in aqueous solutions containing varying concentrations of $\beta$-galactosidase. The strips were read on a Seralyzer ® reflectance photometer at 750 nm after 40-60 seconds. A plot of reflectance data -vs- enzyme concentration revealed a liner dose response over a range of enzyme concentrations from 0.0 to 0.15 units of $\beta$-galactosidase per milliliter.

What is claimed is:

1. 2H-Dibenz[b,f]azepin-2-one based compounds characterized by the formula:

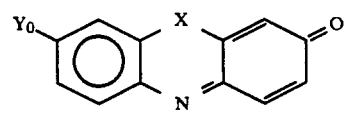

wherein X is CH$_2$CH$_2$or CH=CH and Y is H or an enzyme cleavable group.

2. The compounds of claim 1 wherein Y is an enzyme cleavable group selected to confer specificity to a specific corresponding enzyme.

3. The compounds of claim 2 wherein Y is a sugar or derivative thereof, an acyl group, an amino acid, a peptide or an inorganic acid.

4. The compounds of claim 3 wherein the acyl group is an aliphatic or aromatic carboxylic acid.

5. The compounds of claim 3 wherein Y is an N-protected amino acid.

6. The compounds of claim 5 wherein the N-protected amino acid is N-tosyl-L-alanine.

7. The compounds of claim 3 wherein the peptide contains from 2 to 5 amino acid units.

8. The compounds of claim 3 wherein the inorganic acid is phosphoric or sulfuric acid.

9. The compounds of claim 3 wherein the sugar is a glycosidic radical.

10. The compounds of claim 9 wherein the glycosidic radical is a radical derived from $\beta$-D-galactopyranose, $\alpha$-D-galactopyranose, $\beta$-D-glucopyranose, $\alpha$-D-glucopyranose, $\alpha$-D-maunopyranose, N-acetylglucosamine or N-acetylneuraminic acid.

11. The compounds of claim 9 wherein Y is a radical derived, from an oligosaccharide chain of from about 2 to 20 monosacchaeide units.

* * * * *